United States Patent [19]

Grandone

[11] Patent Number: 5,289,385
[45] Date of Patent: Feb. 22, 1994

[54] ADAPTIVE SCHEDULING SYSTEM AND METHOD FOR OPERATING A BIOLOGICAL SAMPLE ANALYZER WITH VARIABLE RINSING

[75] Inventor: Cass J. Grandone, Lake Forest, Ill.

[73] Assignee: Abbott Laboratories, Abbott Park, Ill.

[21] Appl. No.: 710,195

[22] Filed: Jun. 3, 1991

[51] Int. Cl.$^5$ .............................................. G06F 15/46
[52] U.S. Cl. ...................................... 364/497; 422/67
[58] Field of Search .................. 364/497, 496; 73/863, 73/863.01, 863.11; 422/67, 65; 436/34, 50, 47, 48

[56] References Cited

U.S. PATENT DOCUMENTS

| | | |
|---|---|---|
| 3,497,320 | 2/1970 | Blackburn et al. |
| 3,597,161 | 8/1971 | Greiner |
| 3,660,638 | 5/1972 | Oberli ................................. 422/66 |
| 3,728,080 | 4/1973 | Moran |
| 3,770,382 | 11/1973 | Carter et al. |
| 3,799,744 | 3/1974 | Jones |
| 3,874,850 | 4/1975 | Sorensen et al. .................. 422/64 |
| 4,054,416 | 10/1977 | Duff ..................................... 422/64 |
| 4,058,367 | 11/1977 | Gilford ................................ 422/63 |
| 4,113,436 | 9/1978 | Werder et al. ..................... 422/65 |
| 4,265,855 | 5/1981 | Mandle et al. .................... 422/65 |
| 4,303,611 | 12/1981 | Jessop ................................ 422/65 |
| 4,326,851 | 3/1982 | Bello et al. ..................... 204/153.1 |
| 4,370,983 | 2/1983 | Lichtenstein ...................... 128/630 |
| 4,383,041 | 5/1983 | Kutsusawa et al. .............. 435/291 |
| 4,416,995 | 11/1983 | Amaral .............................. 435/291 |
| 4,595,562 | 6/1986 | Liston et al. ....................... 422/65 |
| 4,603,114 | 7/1986 | Hood et al. ........................ 436/89 |
| 4,655,225 | 4/1987 | Dähne et al. ...................... 128/633 |
| 4,678,752 | 7/1987 | Thorne et al. .................... 435/291 |
| 4,795,613 | 1/1989 | Azuma et al. ..................... 422/64 |
| 4,796,197 | 1/1989 | Lissot et al. ....................... 364/500 |
| 4,835,110 | 5/1989 | Seymour et al. .................. 436/517 |
| 4,935,875 | 6/1990 | Shah et al. ......................... 364/497 |
| 4,971,900 | 11/1990 | Ahnell et al. ...................... 435/29 |
| 4,995,402 | 2/1991 | Smith et al. ...................... 128/771 |
| 5,122,342 | 6/1992 | McCulloch et al. .............. 422/65 |
| 5,139,743 | 8/1992 | Ishizaka et al. ................... 422/63 |
| 5,154,889 | 10/1992 | Muraischi ......................... 422/65 |
| 5,158,895 | 10/1992 | Ashihara et al. ................. 436/526 |
| 5,175,086 | 12/1992 | Takekawa et al. ............... 435/7.92 |

OTHER PUBLICATIONS

"ADx ® System Operator's Guide", by Abbott Laboratories, Diagnostics Division, 1987, 1988, 1989, 1990, pp. R-105 19 to R-105 26; R-105 2-10; R-105 4-4; and R-105 4-10 to R-105 4-45.

Primary Examiner—Jack B. Harvey
Assistant Examiner—Thomas Peeso
Attorney, Agent, or Firm—Richard D. Schmidt

[57] ABSTRACT

An improved biological sample analyzer for conducting assays of samples loaded therein, and a method and system for operation thereof, that schedules operations by instrument systems on each biological sample and schedules a conditional cleaning operation prior to a scheduled instrument system operation. The analyzer conducts the assays of the biological samples by performing the scheduled instrument system operations and performs a cleaning operation prior to any scheduled instrument system operation conditioned upon the instrument system operation scheduled prior to the cleaning operation. The biological analyzer can perform a warming operation prior to a scheduled instrument system operation determined upon the lapse of time between the scheduled instrument system operation and the instrument system operation scheduled prior thereto.

29 Claims, 5 Drawing Sheets

Microfiche Appendix Included
(2 Microfiche, 139 Pages)

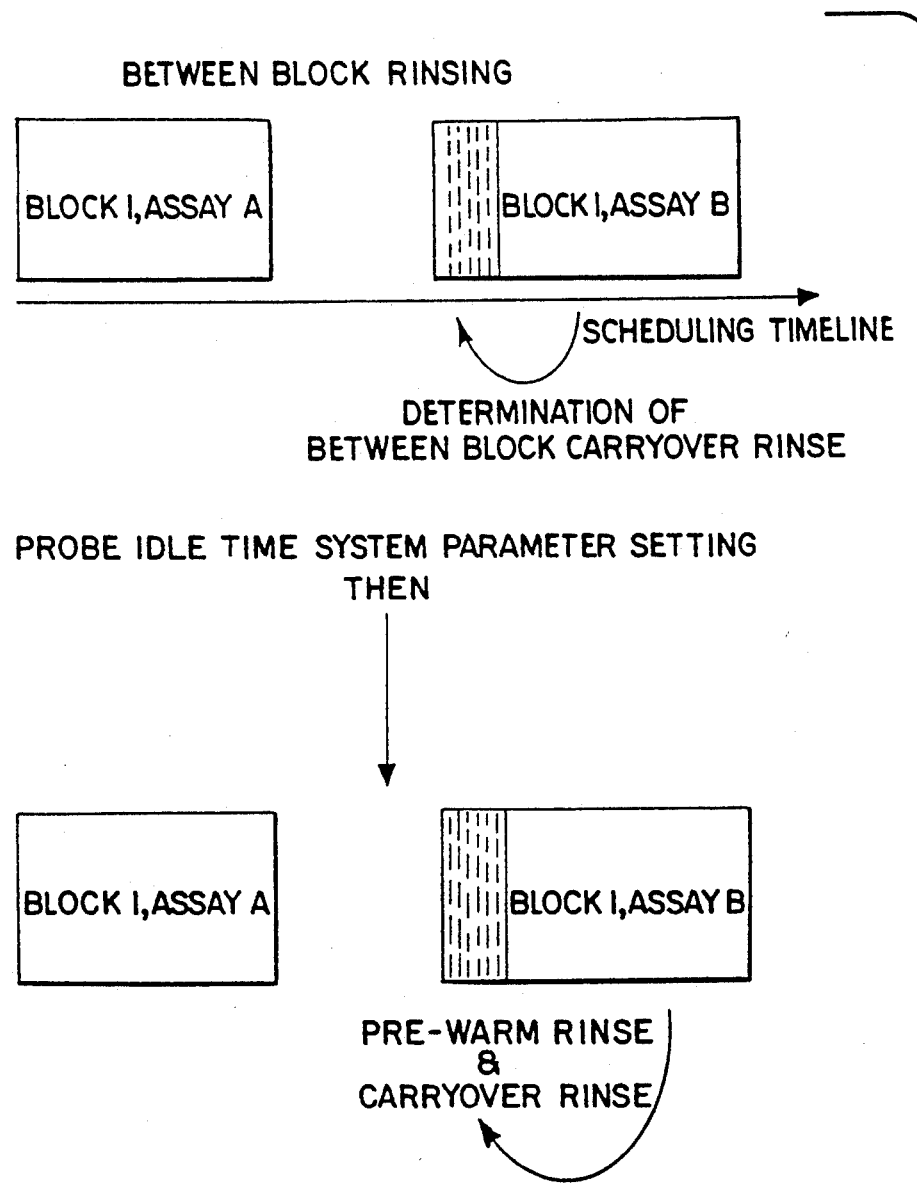

ADAPTIVE SCHEDULING SYSTEM AND METHOD FOR OPERATING A BIOLOGICAL SAMPLE ANALYZER WITH VARIABLE RINSING

MICROFICHE APPENDIX

Included are two microfiche of 139 total frames.

REFERENCE TO RELATED APPLICATIONS

The disclosures of the following copending applications assigned to the assignee of the present application and filed concurrently herewith are specifically incorporated by reference:

"Adaptive Scheduling System and Method For Operating a Biological Sample Analyzer With Variable Interval Periods", by Kathy Burns, Ilya Ratner, Jeanine T. Douglas, Erica Kline, and Cass J. Grandone Ser. No. 07/709,723, filed Jun. 3, 1991;

"Adaptive Scheduling System and Method For a Biological Analyzer With Reproducible Operation Time Periods", by Cass J. Grandone, Mark Pierce, Ilya Ratner, and Jeanine T. Douglas Ser. No. 07/709,721, filed Jun. 3, 1991;

"Retrofit Kit For Changing Single Immunoassay Instrument to Flexible Multiple Immunoassay Instrument", by Chadwick M. Dunn, Cass J. Grandone, Stephen L. Herchenback, Robert J. Nelson, Robert Perry, James T. Tyranski and Gary Lee Zuck Ser. No. 07/709,730, filed Jun. 3, 1991;

"Carousel For Assay Specimen Carrier", by Cass J. Grandone, Steven L. Herchenback, Robert Perry, James T. Tyranski and Gary Lee Zuck Ser. No. 07/709,726, filed Jun. 3, 1991;

"Heat and Air Flow Control For Assay Carrier", by Chadwick M. Dunn, Cass J. Grandone, James T. Tyranski and Kris T. Luddington Ser. No. 07/709,728, filed Jun. 3, 1991;

"Reagent Bottle and Cap", by James T. Tyranski Ser. No. 07/709,725, filed Jun. 3, 1991; and "Reagent Pack For Immunoassays", by Steven Herchenback, Robert Nelson, James T. Tyranski and Gary Lee Zuck Ser. No. 07/709,726, filed Jun. 3, 1991.

BACKGROUND OF THE INVENTION

The present invention relates generally to biological sample analyzers used to perform assays of patient specimen samples. More particularly, the present invention relates to a method and system for the scheduling an adaptive rinse operation as part of the operating steps for performing assays of biological samples in an automatic analyzer.

Biological sample analyzers, of the type considered herein, are automated instruments that may be used in hospitals, clinics, laboratories, or other locations, to run routine tests (assays) on samples of patient specimens such as blood, spinal fluid, urine, serum, plasma, and so on. An automated analyzer of the type discussed herein includes an analyzer unit that runs tests on a number of patient specimen samples that are loaded into the unit. An operator-user prepares the samples by placing portions of the patients' specimen samples into a number of like-sized sample containers. These samples may be diluted or otherwise treated, depending upon the type of analyzer used, the type of assay being performed, and other factors. The containers are then placed in the analyzer unit. The containers may first be placed in a rack or carousel that is then placed in the analyzing unit. The rack may accommodate a number of sample containers, e.g. 24. In addition, one or more appropriate chemical reagents, needed to perform the assays, are also placed in the analyzer unit. In order to mix reagents with the samples, the analyzer unit may also include a fluid moving system, such as a robotic probe mounted on a boom, which is adapted to draw up portions of the reagents and/or samples and expel them into appropriate locations, e.g. additional cells such as reaction cells provided in the sample containers, where a reaction can take place. The analyzer unit also may include a means for detecting a reaction in the reaction cells. This may include an optical detector to observe fluorescence reactions and make optical measurements to obtain a result for each sample. The analyzer unit may also typically include other mechanical systems to move the sample containers and the probe. The analyzer unit may also provide for cleaning the probe between certain tasks in order to avoid contamination between samples. For this purpose, the analyzer unit may also include a washing station and a waste dispensing container to hold the used rinse solution. (For purposes of this specification and claims, the terms "rinse" and "cleaning solution" are used interchangeably).

After the operator-user loads the specimen samples, enters appropriate instructions, and starts the unit, the analyzer runs unattended. When placed in operation, the analyzer unit, using the appropriate chemical reagent, runs the same test on each of the samples in the sample containers and will perform identical operations on each of the samples loaded in the rack. When it is finished, the analyzer prints out or otherwise reports on the results of its testing.

Biological analyzers utilize different chemistries for performing assays of specimen samples. One type of assays used in biological analyzers includes immunoassays and solid phase procedures. Analyzers for performing immunoassays in general and enzyme immunoassays in particular are known in the art.

A biological analyzer that utilizes immunoassay chemistry to perform assays of specimen samples loaded therein is the IMx ® analyzer introduced in 1988 by Abbott Laboratories, of North Chicago, Ill. (A description of the IMx analyzer is included in "The Abbott IMx Automated Benchtop Immunochemistry Analyzer System", by Fiore, M. et al., *Clinical Chemistry*, Vol. 34, No. 9, 1988, which is specifically incorporated herein by reference in its entirety). The IMx analyzer is a biological sample analyzer that has been developed for use in conjunction with solid phase immunoassay procedures to perform a variety of assays (such as sandwich and competitive assays). The IMx analyzer uses a technology referred to as microparticle capture enzyme immunoassay (MEIA) and fluorescence polarization immunoassay (FPIA). The IMx analyzer includes a microprocessor used to control a robotic arm with 2 degrees of freedom and a rotating carousel to process the samples for assay. One assay can be done on each of 24 specimen samples in 30–40 minutes or more unattended after loading (i.e. with "walk away" automation). Assay results are output to a printer or a computer interface.

A biological sample analyzer, such as the IMx analyzer described above, can execute the steps required for performing assays of up to 24 specimen samples, including the steps of counting the samples, identifying which assay to run, warming the reagents and reaction cells to appropriate temperatures, pipetting the reagents and samples, diluting samples if required, timing critical assay steps such as incubations, washing unbound conjugate, quantifying the fluorescence signal and performing data reduction to yield a useful result.

The container used for holding each of the specimen samples for a biological sample analyzer, such as the IMx analyzer, may be a disposable assay cartridge having a plurality of wells, with at least one reaction well and one separation well. The separation well may contain a fibrous matrix positioned across its entrance and an absorbent material positioned below the fibrous matrix. Microparticles react with an analyte containing sample and one or more reagents to form a complex. This complex is immobilized on the matrix of the separation cell. The excess sample and reagent are washed through the matrix and captured in the absorbent material below.

The results of the reactions may be read using known optical detection techniques. For example, using conventional solid phase procedures, an analyte can be labeled or tagged with an enzyme which in the presence of its substrate fluoresces and emits light at a known wave length. The rate at which the fluorescent product is produced is indicative of the concentration of the analyte in the biological sample. A conventional fluorometer is suitable for illuminating the fibrous matrix with a beam of light having the appropriate excitation wave length. The fluorometer also detects the intensity of the light at the emission wave length assays. Using this type of solid phase technology has been found to provide a high degree of sensitivity.

A biological sample analyzer, such as the IMx analyzer, provides for performing assays of patients' specimen samples and reading the results of such assays in a mass production type manner. This allows such assays to be made available quickly and conveniently.

The steps that the instrument systems follow to perform the assay in the biological analyzer are included in a program called a protocol. The protocol is written by an assay developer and may be included on the module. The protocol is a series of steps or instructions for the instrument systems to perform including time constraints on when the steps are to be performed. These steps could include mixing the sample with one or more reagents in a mixing cell, providing an incubation time, and measuring a reaction. Often, certain steps for each sample have to be separated by an incubation time to allow for a reaction to take place. Instrument systems, such as the probe, may perform some of the steps for one specimen sample until an incubation time is needed and then the probe performs a similar series of operations on another of the specimens, and so forth. When moving from one sample to the next, the probe may have to be decontaminated to prevent carryover by inserting it into a rinse solution. Commands to perform a rinse operation are included in the protocol. With this type of operation, the assay developer would typically write an instruction in the assay protocol to clean the probe after a series of operations to prevent contaminating the next sample. Because the types of samples and reagents is known to the assay developer, the assay developer could instruct the analyzer to perform a cleaning operation appropriate to clean the probe to prevent carry over. Different cleaning operations are necessary depending upon the type of specimens and reagents being handled. For example, it might be determined that the probe would be sufficiently cleaned by drawing into it a certain number of ml of the rinse solution and expelling the rinse. For other specimens and reagents, it may be necessary to perform the cleaning operation twice. Alternatively, it may be necessary to draw the rinse into the probe and hold it for a certain number of seconds. In a biological analyzer, such as the IMx analyzer, dozens of different types of rinses may be used depending upon the needs of assay.

Even though such analyzers can provide significant advantages by performing assays quickly and conveniently, further advantages for the user could be obtained if the overall through put of the analyzer could be increased. One way to provide even more advantages and convenience for users of biological analyzers would be to provide the capability to perform more than one assay on the specimen samples in an unattended run. Although a biological analyzer such as the IMx analyzer can perform different types of assays and can perform assays on a number of specimen samples unattended, the analyzer can run only one type of assay at a time. If a different type of assay is to be performed, the analyzer would have to be reloaded with different reagents. Also, because different types of assays may require different amounts of the sample specimen, different amounts of reagents, different processing steps, different incubation times, etc., the analyzer would also be reset at the beginning of the run to perform the new assay. In the case of the IMx analyzer, a different memory module may have to be inserted containing the instructions for the analyzer unit for performing the different assay. Thus, even if only a few of several different types of assays need to be run, the operator-user has to load and run the analyzer for the first type of assay for only a few samples and then reload the analyzer to run the second type of assay on another batch of samples using perhaps different reagents. It is recognized that for many users of the IMx analyzer, or other biological sample analyzers, it would be convenient and advantageous to be able to perform more than one type of assay during an unattended run.

Although analyzers having the capability to perform more than one assay in an unattended run have the potential to provide further advantages and convenience for the operator-user, when the operator-user is given the capability to choose which type of assays to perform in an unattended run, providing this feature presents several obstacles relating to the analyzer operation. One obstacle associated with operating an analyzer to perform more than one assay in a run relates to carryover. In the prior analyzers that perform only one assay in an unattended run, the developer could readily determine the sequence of operating steps and provide the appropriate instruction in the protocol for the type of cleaning operation, such as rinse, needed to prevent carryover. However, in an analyzer in which more than one assay is being performed, there is a large number of possible permutations of load list combinations available. For example, if there are 24 specimen samples in the carousel rack and the operator-user is permitted to select any one of three different assays to be performed on the samples, there are almost 2500 different permutations of possible combinations of assays and samples that the user can select. If the operator-user is permitted to select any one of four different assays to be performed on the 24 samples, there are approximately 10,000 different permutations of possible combinations. Thus, the assay developer is no longer able to know with certainty which samples will be handled by sequential operations of the analyzer instrument systems, such as the probe or which reagents will be used for subsequent operations or even which operations will be performed sequentially. For example, the potential exists for an analyte to be present in a sample upon which an assay not specific to that analyte is performed to be carried over to a sample upon which an assay specific to that analyte is being performed thereby causing a false positive. Whereas in single assay runs, the assay developer could predict with a certainty the type of rinse needed to avoid contamination, with the load list combinations present with more-than-one assay runs, the number of permutations of possible operating sequences is high enough that it becomes difficult to predict the type of rinse operation is required.

One way to address this concern is to establish a rinsing safety factor high enough to always effectively clean the probe regardless of the sequence of operations. Thus, the assay developer would use a strong rinse or a large quantity or duration of rinse between all operating steps. This rinse would be based upon the worst case contamination concern. If the worst case contamination were always provided for, the analyzer would use a considerable amount of rinse and would likely be using more rinse than is needed between instrument system operations for many load list permutations.

Using more rinse than is necessary is inconvenient and requires the refilling the cleaning solution container frequently. Using more rinse than is necessary requires disposing of the large quantity of rinse waste generated. Moreover, excess rinse can lead to problems. For example, if too much of a certain rinse is used and some of it carries over to another sample for another assay that is sensitive to that rinse, it may interfere with the chemical reactions in performing the assay for the latter sample.

Another problem related to operating an analyzer to perform more than one assay in a run relates to warming the probe. As mentioned above, assays and particularly immunoassays are sensitive to the temperature. For that reason, provision is made to stabilize the temperature as much as possible. When operating an analyzer with more than one assay type and the high number of possible combinations of operations, it is possible that the probe may be idled for a period of time and possibly cool off. one way to ensure that this does not happen is by inserting the probe into the rinse which is maintained at a preferred temperature. This operation is referred to as "pre-warming". In an analyzer that performs more than one assay and that has a high number of possible combinations of operating steps, it cannot readily be determined when such a pre-warming step should be performed if at all.

Accordingly, it is an object of the present invention to provide a biological sample analyzer, and a method and system for operation thereof, that provides for a cleaning operation to prevent carryover and a pre-warming operation when needed, especially when more than one type of assay is performed on patient specimen samples loaded therein.

It is a further object of the present invention to provide for a variable cleaning operation sufficient to prevent contamination of the fluid handling systems and which reduces excessive waste and improves through put.

SUMMARY OF THE INVENTION

The present invention provides for an improved biological sample analyzer for conducting assays of samples loaded therein, and a method and system for operation thereof, that schedules operations by instrument systems on each biological sample and schedules a conditional cleaning operation prior to a scheduled instrument system operation. The improved analyzer conducts the assays of the biological samples by performing the scheduled instrument system operations and performs a cleaning operation prior to any scheduled instrument system operation conditioned upon the instrument system operation scheduled prior to the cleaning operation. The biological analyzer can perform a warming operation prior to a scheduled instrument system operation determined upon the lapse of time between the scheduled instrument system operation and the instrument system operation scheduled prior thereto.

For purposes of this specification and claims, it is understood that a cleaning operation in an analyzer of the type considered herein is typically performed by rinsing the probe of the analyzer in a cleaning solution or by aspirating a portion of cleaning solution with the probe or by other by operations. Reference to a cleaning operation shall be considered to include any of these types of rinsing operations. Rinsing operations may also be considered to include other types of cleaning operations.

For purposes of this specification and claims, a "run" is considered to refer to the operation of the analyzer in performing the assays after the operator-user has loaded into the analyzer the specimen samples, reagents, rinse, or other accessory material and also entered any necessary information pertaining to the assays to be performed on the samples. The "run" concludes when the assays have been performed on all the samples and may include data analysis performed in generating an assay test result or printing or otherwise outputting the results of the assays. In automatic analyzers of the type considered herein, the run may proceed unattended.

BRIEF DESCRIPTION OF THE FIGURES

FIG. 8 is a diagram of the portion of the program performed by the STAGE 3 procedures of FIG. 4 for determining the adaptive cleaning operation or pre-warm operation appropriate for a time block.

DETAILED DESCRIPTION OF THE PRESENTLY PREFERRED EMBODIMENTS

Figure 1:
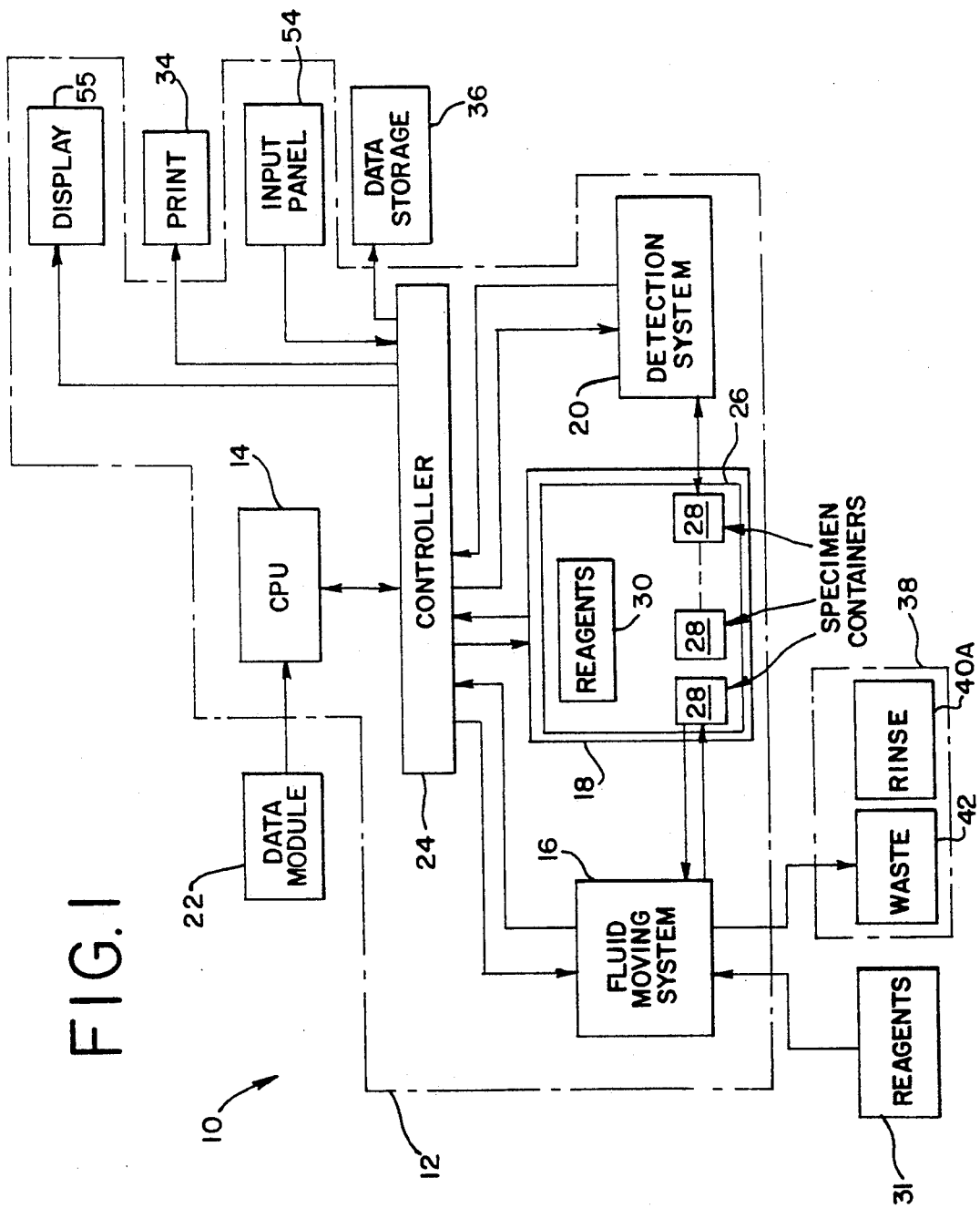
FIG. 1 is schematic of a biological sample analyzer incorporating aspects of a first presently preferred embodiment of the present invention. .

Referring to FIG. 1, there is depicted a schematic block diagram of a biological sample analyzer 10 of a first embodiment of the present invention. The biological system analyzer 10 includes an analyzer unit 12, in which is included a CPU 14. The CPU 14 operates analyzer unit instrument systems in accordance with means well known to those skilled in the art. The analyzer unit instrument systems include a fluid moving system 16, a carousel moving system 18, and a detection system 20. Additional systems may also be included. One or more modules 22 include programming, stored for example in a PROM, used for the operation of the analyzer unit 12 and the analyzer unit systems. The programming on these modules 22 may include separate programs (called protocols, described in more detail below) specifically adapted for performing specific different types of assays. These modules 22 may be removable to provide for additional different assays to be performed as well as to readily provide for updates and improvements to the system operation to be implemented. The analyzer unit instrument systems 16, 18 and 20 operate through an appropriate controller-interface 24. In this embodiment, the CPU 14 used is an Intel Model 80286 microprocessor.

The carousel moving system 18 is adapted to move a carousel or rack 26 upon which is positioned a plurality of patient specimen sample containers 28. The carousel 26 is preferably removable in order to facilitate loading and unloading of the patient specimen sample containers 28 into the analyzer unit 12. The carousel 26 may also hold a first set of one or more reagents 30 for performing a particular assay. A second set of one or more reagents may also be included in the analyzer unit 12 in a location off of the carousel 26. These reagents may be in reagent packs and may include reagents for performing MEIA and/or FPIA types of assay tests, as described above.

The fluid moving system 16 includes one or more robotic pipette-booms adapted to move fluid from one location to another in the analyzer unit 12, e.g. from one container to another, under the control of the CPU 14.

The CPU 14 operates the carousel moving system 18 to move the carousel 26 and the fluid moving system 16 to move the pipette-boom to mix the appropriate reagents with the specimen samples in the containers 28. The CPU 14 also operates the carousel moving system 18 to move the carousel 26 and thereby the containers 28 into position to observe reactions at the detection system 20. The CPU 14 controls the detection system 20 which may include means for detecting florescence in a manner that is well known in the art. In a preferred embodiment, the detection system 20 includes a low pressure mercury lamp used in a fluorometer. The CPU 14 receives the information about the reactions from the detection system 20 and performs the appropriate data analysis, and outputs results to either a printer 34 or to a data storage 36. A cleaning station 38 may also be provided in the analyzer unit 12. The cleaning station 38 includes a rinsing solution 40A and a waste container 42 into which waste fluid can be dispelled.

Figure 2:
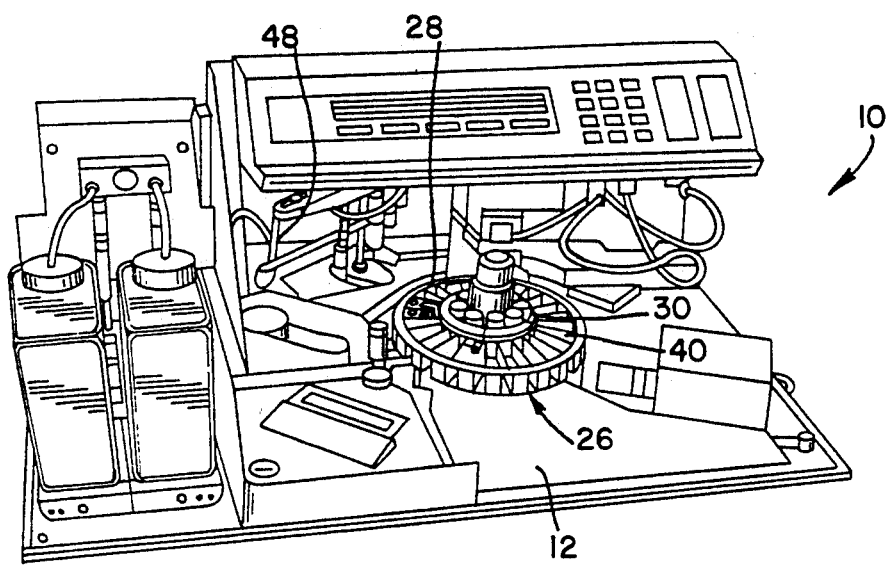
FIG. 2 is perspective view of a biological sample analyzer (with a cover portion removed to reveal components therein) of the embodiment of FIG. 1.

FIG. 2 depicts a perspective view of the biological sample analyzer 10, partially disassembled, incorporating aspects of the first embodiment of the present invention. The analyzer unit 12 holds the circular carousel rack 26 into which are placed a plurality of assay container cartridges 28. These cartridges 28 are preferably disposable. The assay container cartridges 28 are placed in a plurality of openings 40 (also referred to as "wedges") arranged around a central core of the carousel rack 26 which is specially formed to hold the cartridges. All the cartridge containers 28 have individual alignment features that insure their accurate alignment within the rack 26.

The carousel rack 26 containing the cartridge containers 28 can be circularly indexed to accurately position each assay cartridge container relative to the detection system 20 containing an optical reading apparatus. Because the reading positioning is highly accurate, the assay is properly positioned for reading at a reading station.

The fluid moving system 16 includes a pipette/probe assembly that include syringes 48 (e.g. a 250 microliter sample syringe and a 2500 microliter diluent syringe may be provided) driven by stepper motors. The pipette/probe assembly can be positioned over the reagents 30, the individual cells of the containers 28, or the wash station 38. Stepper motors move the pipette system up and down as well as radially. The fluid moving system 16 transfers fluid from reagent bottles to separation wells and from well to well. The pipette itself is a drawn stainless steel tube, teflon coated to minimize carryover. Fluid levels may be sensed by measuring electrical conductivity between the pipette probe tip and an electrode.

Carryover between samples and reagents is minimized by washing the pipette/probe over a wash station.

Because enzyme immunoassays require precise temperature control to achieve repeatable performance, heating elements (not shown) are provided in the analyzer unit 12.

The biological analyzer 10 illustrated in FIG. 2 is similar to the prior analyzer (the IMx analyzer) sold by Abbott Laboratories, Inc. Compared to the prior analyzer, this embodiment of the analyzer includes additional reagents 30 that are stored in the carousel 26 in the analyzer and are used to perform the greater-than-one assays during a run. The description of the details of construction of the analyzer are disclosed to help define the environment of the present invention and such details do not form part of the invention. This embodiment of the analyzer also includes additional programming to perform the greater-than-one assays during a run.

Figure 3:
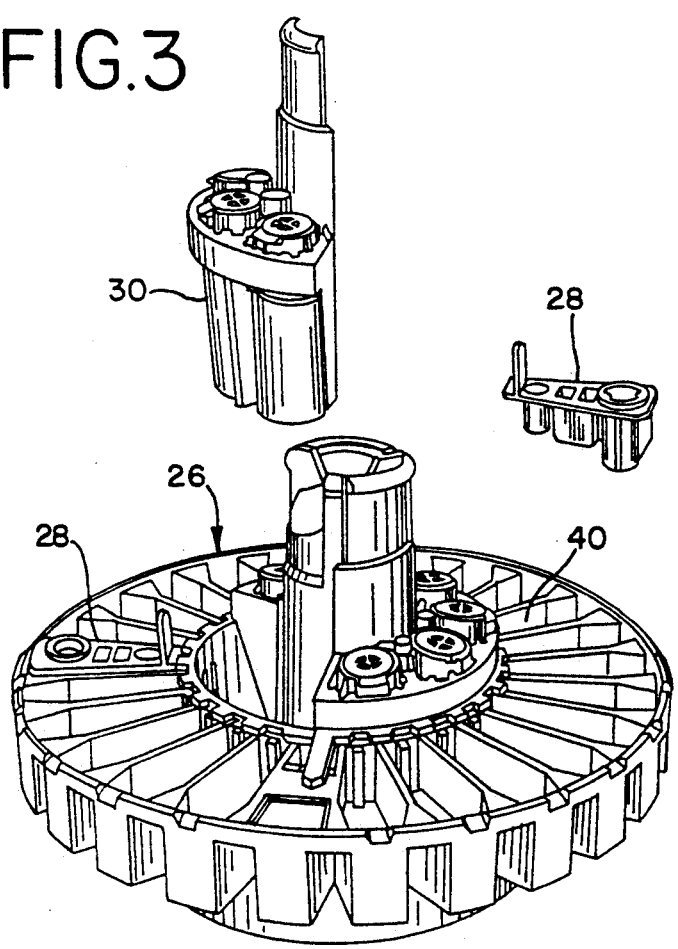
FIG. 3 is a perspective view of the carousel rack of the embodiment shown in FIG. 2.

As shown in FIG. 3, a first set of reagents 30 is included on the carousel 26. In a preferred embodiment, these reagents 30 are included on a portion of the carousel 26 and located centrally of the sample wedges 40.

An operator-user prepares for an assay run sequence by loading containers containing patient specimen samples (sometimes referred to as "disposables") into the carousel 26. In this embodiment, approximately 150 microliters of sample, controls, or calibrators is added to a sample well of each of the reaction cells of the container. The carousel rack is then placed in the analyzer unit 12 and the appropriate reagent pack or packs are loaded into the unit or the carousel.

In this embodiment of the analyzer 10, the operator-user also includes a calibration sample for each assay type being run. Thus, if three different types of assays are being run, three separate calibration samples are also run. The calibration samples have a known amount of the substance being tested for, and accordingly, are used as a basis for determining the amounts of the tested for substance in the unknown specimen samples by comparison of the reactions. This use of calibration samples is similar to what has been performed in the prior IMx analyzer. Typically, the calibration samples occupy specific positions (i.e. wedges) in the carousel rack 26.

The operator-user enters a load list. This may be done by means of the input panel 54 (of FIG. 1). The entry of the load list may be prompted by a menu on the display 55. The load list identifies the wedges of the carousel in which patient specimen samples are located and which assay is to be run on each of the specimen samples. Not all of the wedges of the carousel have to be used. The operator-user has the option of selecting several different assays to be performed automatically in a single run and also has the option of selecting the number of specimen samples to be used for each different assay. In a preferred embodiment up to four different assays may be available, however, the present invention could be extended to even a greater number. In a preferred embodiment, the samples upon which the same assay is to be performed are grouped together, i.e. in adjacent wedges of the carousel. This facilitates input of the load list by allowing the operator-user to indicate at which wedge position the specimen samples for a specific assay begin.

For purposes of efficiency, certain types of assays will be typically grouped together. For example, the assays for Prolactin, LH and FSH will be typically grouped together and the tests for CEA, AFP, and CA 19-9 will be grouped together. Other grouping of assays can be provided. These grouping are based, in part, upon the likelihood that an operator-user would want to run these assays at the same time. These combinations could be changed to include other assays or delete assays if different combinations would be preferred. If a different combination of assays were included, the appropriate reagents for those assays would be loaded in the analyzer unit.

Although in a preferred embodiment, the user-operator enters a load list by inputting information into the input panel 54, the load list for a run may be entered by other means. For example, the load list could be entered via a computer or communications interface. Alternatively, the load list may be determined automatically by scanning information attached or otherwise associated with each specimen sample container.

After closing a door or otherwise performing any other steps for preparing the analyzer unit, the operator-user actuates a run button on the input panel 54 of the analyzer unit. From this point, the analyzer can operate automatically and unattended until all the assays are finished.

Under the control of a program run on the CPU 14, the analyzer unit 12 begins a preparation process in which the following actions typically are taken: all stepper motors (fluids, syringe pumps, carousel motor, pipette system motors) are "home" (adjusted to times 0), the carousel rack is scanned to identify the type of carousel installed and its "lock" status. The reagent pack types may be read by a bar code scanner located on the pipette system to identify or confirm the assays to be run. The carousel heating systems warm the reagents and reaction cells to the appropriate temperatures by directing heated air throughout the carousel as described in the copending application referred to above. The program also calls a scheduling program that schedules the operations to be performed by the instrument systems on the specimen samples.

Figure 4:
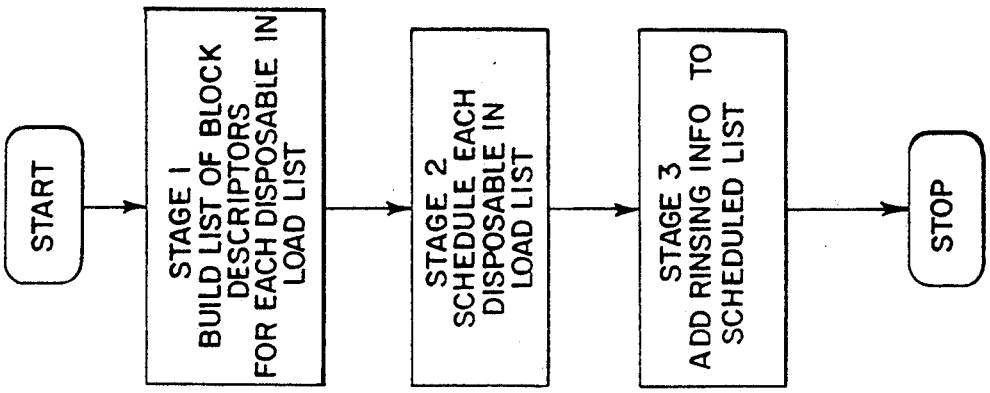
FIG. 4 is a block diagram flow chart depicting operating stages of a scheduler routine for operating the embodiment of the invention shown in FIG. 1.

FIG. 4 is a flow chart illustrating the program operation for the scheduler program 60 used to schedule the operations to be performed by the analyzer unit to perform the assays on the load list in accordance with one embodiment of the present invention. The scheduler program allows for scheduling the tasks performed by the analyzer in order to assure that certain tasks are performed within allowable time frames and with favorable through put. STAGE 1 includes procedures for creating a list of time blocks and block descriptors for each time block, estimating the running time for each block, and sorting the load list. STAGE 2 includes procedures that establish the schedule of time blocks for each specimen sample so that the operations of a time block of a sample being scheduled do not conflict with any time blocks of any samples that have already been scheduled and that incubation limits between time blocks are not exceeded. STAGE 3 includes procedures for scheduling the cleaning or warming operations in, between, or before time blocks.

Figure 5:
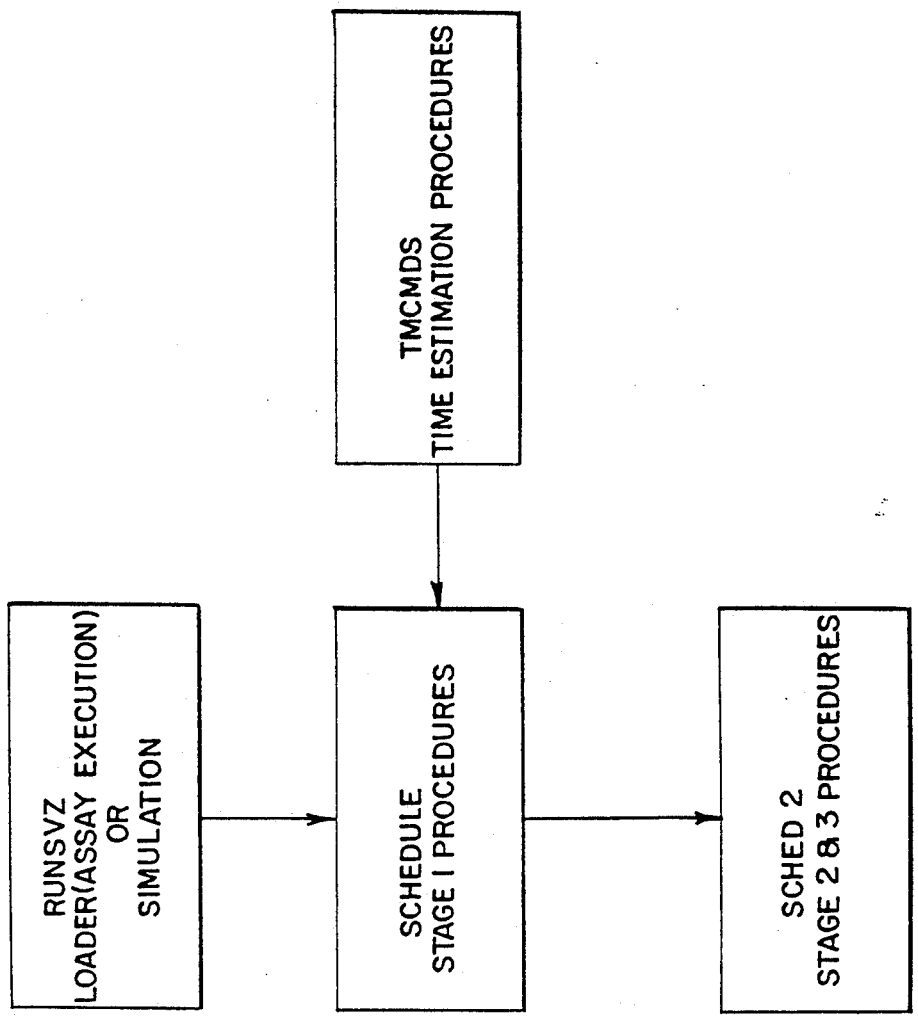
FIG. 5 is a block diagram flow chart depicting a portion of the program routines included on the module for operation of the embodiment of FIG. 1.

FIG. 5 is a flow chart illustrating the program routines for operating the analyzer and calling the scheduler routines. A first routine RUNSVZ begins the operation and performs certain initialization procedures. RUNSVZ calls the SCHEDULE program that includes the STAGE 1 procedures. Time estimations for performing the "blocks" of commands are developed in the TMCMDS routine and output to the SCHEDULE program. The SCHEDULE program calls the SCHED2 program that includes STAGE 2 and STAGE 3 procedures. TMCMDS.LST, SCHEDULE.LST, and SCHED2.LST, are included in Appendix 1 of this specification.

Figure 6:
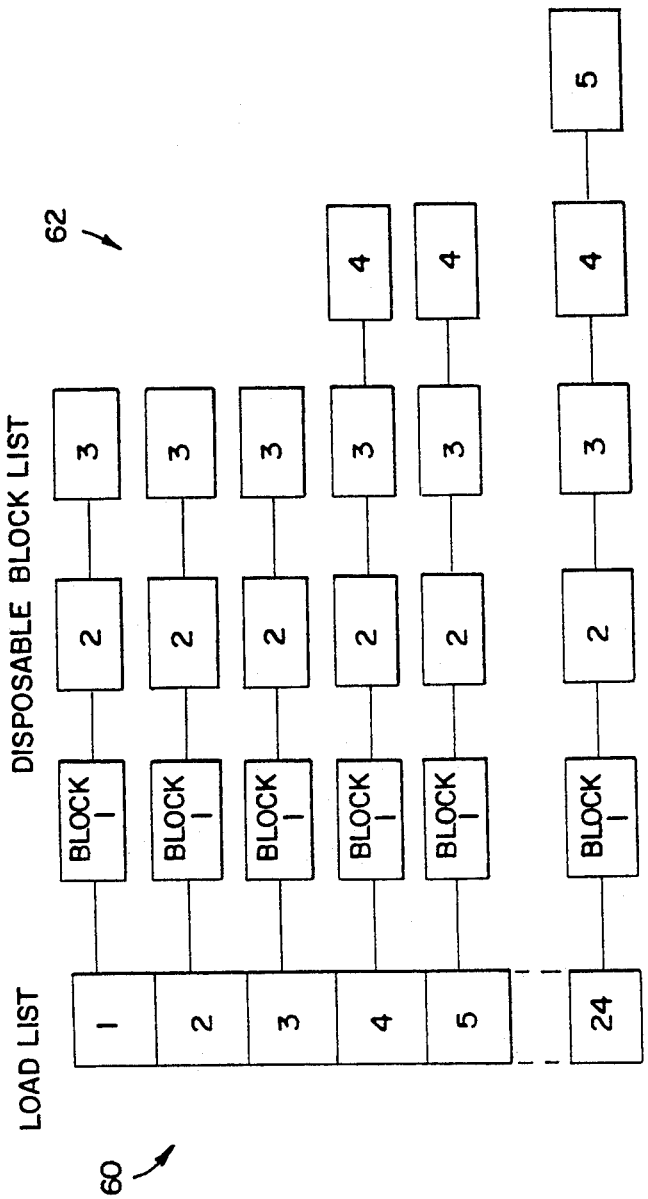
FIG. 6 is a diagram showing correspondence between a load list and lists of block descriptors associated with each specimen sample as developed by the STAGE 1 procedure of FIG. 4.

FIG. 6 is a diagram showing correspondence between the load list 60 and lists of block descriptors associated with each specimen sample as developed by the STAGE 1 procedures of FIG. 4. Based upon the entered load list, the STAGE 1 procedures develop time allowances for the operations to the performed by the analyzer unit instrument systems upon each specimen sample. The load list 60 indicates the sample specimen, e.g. Samples 1–24. The time allowances are organized into "time blocks", 1, 2, 3, associated with each of the samples. The time blocks represent one or more operations or activities to be performed by the analyzer systems upon or for that sample. Each specimen sample typically has associated with it several time blocks. For example, Sample 1 (as well as Samples 2 and 3) has three time blocks associated with it, Sample 4 has four time blocks associated with it, and Sample 24 has five time blocks associated with it. According to this embodiment of the invention, the time blocks establish when an analyzer unit resource (e.g. an instrument system) is occupied with a task associated with a sample. Accordingly, only one time block can take place (i.e. be performed) at a time.

As mentioned above, in the STAGE 1 procedures in which the time blocks are developed, each of the time blocks of each specimen sample has "block descriptors" associated with it. The block descriptors contain information such as which sample the block is associated with, how much time will be allowed to perform the steps in this time block, and importantly, whether this block must be performed within a specific time limit or a specific range of time limits of other blocks associated with this sample.

After the STAGE 1 procedures are completed, the scheduler program calls the STAGE 2 scheduler procedures. The STAGE 2 procedures actually develop the schedule of time blocks generated by STAGE 1. The sample having the highest assigned priority sequence number is scheduled first. As mentioned above, the sequence number does not necessarily correspond to which assays are started first, but rather to which samples are scheduled first. It is evident however that the assay for the sample with the highest priority will begin first because it will be scheduled first and there will be no constraints on scheduling the time blocks of the assay for that sample. It is also likely that other assays for samples with high priorities will also tend to be begun sooner.

Referring again to FIG. 4, after the STAGE 2 procedures are completed, including the determination of the minimum intervals between time blocks and the scheduling of the time blocks, STAGE 3 procedures are performed. STAGE 3 procedures include the scheduling of necessary and appropriate rinse operations between time blocks, as explained in more detail below.

Figure 7:
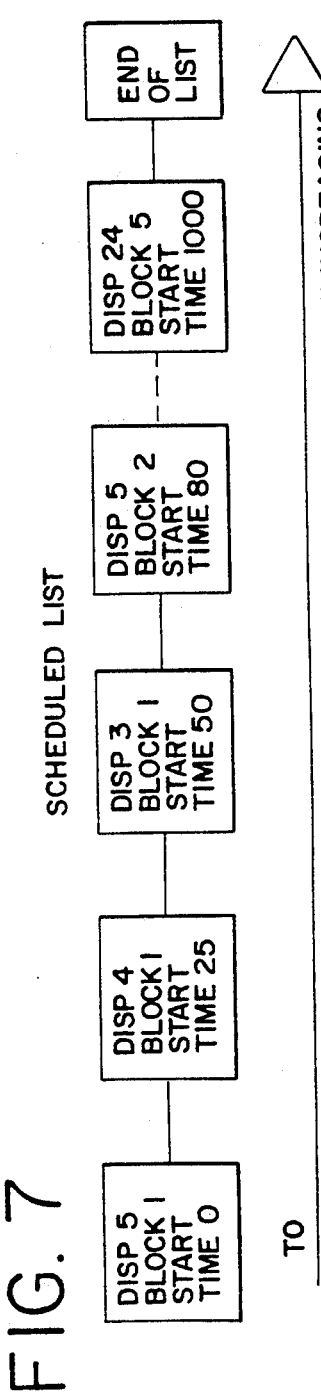
FIG. 7 is diagram depicting an example of a portion of the schedule blocks for all specimen samples to be scheduled and performed by the analyzer of FIG. 1.

Referring to FIG. 7, there is depicted a diagram illustrating an example of a portion of the sequence of time blocks scheduled by the scheduler program, above. Note that a start time has been assigned to each time block. The analyzer can then use the schedule to perform the assays of the specimen samples.

As mentioned above, the cleaning operation is scheduled in the STAGE 3 procedures. It is a feature of this embodiment of the invention that instrument system steps (other than the cleaning operation steps) are scheduled and fixed (in STAGE 2) before the cleaning operation steps are fixed (in STAGE 3). Thus, the determination of the appropriate type of cleaning operation can be made in STAGE 3 based upon instrument system operations that precede as well as follow the cleaning operation.

As mentioned above, in an analyzer of the type considered herein, a time block represents instrument system operations associated with only one specimen. The time blocks are scheduled to perform the assay for each sample and to utilize the time interval between time blocks of one sample to perform time blocks of assays associated with other samples. Therefore, cleaning operations may be considered appropriate at the transition between time blocks because it is at this time that the instrument systems are likely to stop handling one sample and start handling another. However, the type of cleaning operation considered appropriate may depend upon whether different samples are being handled with the same assay or different samples are being handled with different assays. This is because of the greater concern over carryover when going from different sample/different assay than when going from different sample/same assay. Therefore, if the cleaning operations are not fixed until the time blocks for other instrument operations are fixed, then a cleaning operation appropriate for the type of transition between time blocks can be made. Therefore, the schedule of the time blocks that include all the instrument system operations (other than cleaning operations) is first fixed so that it can then be determined from the sequence of scheduled time blocks which type of transition occurs between adjacent time blocks. Then, the appropriate cleaning operation can be scheduled.

In the STAGE 3 procedures, the cleaning operations are fixed. Even though the cleaning operations scheduled are not fixed until STAGE 3, the cleaning operations are based upon the cleaning operation options provided by the protocol written by the assay developer. In preparing a protocol for an assay to be run on an analyzer in which more than one assay can be performed in a run, the assay developer may specify optional cleaning operations one of which will be scheduled and performed depending upon the operations that are scheduled before that cleaning operation. As mentioned above, because of the various schedule permutations, the assay developer does not know specifically which specimens or which assays will be handled before and after the cleaning operation. However, the assay developer does know that it will be one combination out of a number of combinations. Therefore, the assay developer specifies more than one cleaning operation. Then, after the scheduler portion of the program fixes all the time blocks and the assay types and specimens being handled by adjacent time blocks are fixed, the STAGE 3 procedures select the appropriate cleaning operation out of the alternative options provided by the protocol prepared by the assay developer to insert into a final schedule that is performed by the analyzer instrument systems. (Note that in the schedule developed for performing the time blocks in STAGE 2, the rinse execution time must be accounted for in the scheduling process. When there is a conditional rinse to be performed between adjacent time blocks or at the beginning or end of a time block, an appropriate amount of time should be reserved for the rinse operation and this amount of time should be sufficient to perform the alternative rinse operation that required the greatest amount of time.

The principle of operation of this embodiment is demonstrated by reference to the protocol example included in Appendix 2 to this specification. This protocol example provides the instructions for performing the LH assay. The protocol is written in CLI (command line interpreter) which is a high level programming language specifically designed for assay developers for operating the analyzer. By using a high level programming language specifically tailored to operate the analyzer, the assay developer is relieved of the burden of learning to program the detailed analyzer instrument system operations. Instead, the CLI language permits the assay developer to concentrate on the chemistry of the assay. For example, in the protocol example shown in Appendix 2, "MB dilu" means to move the boom to the diluent. "AS" means to aspirate.

In the protocol example of Appendix 2, the commands for performing the instrument system operations are contained within "blocks". Each block begins with the command "B 0" and ends with the command "E". In the preferred embodiment of this invention, all commands for instrument systems operations related to a specimen samples should be included in a time block so that the transition from handling one sample and then another will always correspond to a transition between time blocks and therefore be accounted for. A command for performing a cleaning operation may be specified at or close to the beginning of each block. In practice, a cleaning operation at the beginning of a block is almost always specified. In addition to specifying cleaning operations at the beginning or transition of blocks, the assay developer may also include instructions to perform cleaning operations within blocks, as appropriate.

In the protocol language used, the command "KUSS" is a instruction to perform a cleaning operation. The parameters following the KUSS command specify further information about the cleaning operation. The first parameter is the condition, the second parameter is the type of cleaning operation to be performed and the third parameter is how many times the operation is to be performed. These parameters will be explained in more detail below.

The second parameter of the KUSS command indicates the cleaning operation type. There are various types of cleaning operations that use, for example, different total volumes of rinse, different rinse dispensing speed, different volume/increment and different dispensing heights. In an analyzer of the type considered herein, about 60 different rinse operations are defined and are stored in memory. Each of these different rinse types is given a number. Thus, referring to the example of Appendix 2 at line 2, the cleaning command for the first block is "KUSS 0 24 1". The second parameter, 24, refers to the type of rinse type designated by the number 24 and stored in memory.

The third parameter of the KUSS command indicates the number of repetitions of the specified rinse type to perform. In the example, the third parameter following the KUSS command is "1" which indicates that the specified rinse, i.e. number "24", should be performed one time.

The first parameter following the KUSS command is the conditional trigger. In this embodiment, the numbers "0", "1", and "2" are may be specified. "0" means that the rinse specified in this command should be performed regardless of the block preceding this block in the fixed schedule. "1" means that the rinse specified in this command should be performed if the block preceding this block in the fixed schedule is the same block/same assay only. "2" means that the rinse specified in this command should be used if the block preceding this block is a different block only. Note that if a "1" is specified, "2" must be located immediately after. In this scenario one rinse type is executed in IF THEN ELSE fashion; however, "2" can be specified without "1".

For purposes of the conditions set forth in the conditional rinse commands, "Same Assay/Same Block, or Different Block" means that a Different Block can be the same assay/different block or different assay block.

In a further aspect of the present embodiment, a default rinse is specified. The default rinse is scheduled by the scheduler program but is not listed as a command in the protocol written by the assay developer. This default rinse is used to address the problem of pre-warming the probe. As mentioned above, it is possible that depending upon the combination of assays provided on the load list, that there may be a substantial time between scheduled time blocks when the instrument systems, such as when the probe may be idle. In such a case, it is possible that the probe might cool off while it is idle. Then, when it is used again for the instrument operations of the next scheduled block, it may cool off the reagent or sample being handled thereby affecting the assay. The default rinse accounts for this potential problem by scheduling a default rinse prior to any block when the amount of time after the end of the previous block and before the start of the block exceeds a predetermined time. This time between blocks can be determined after the STAGE 2 procedures schedule all the time blocks. The default rinse in scheduled in STAGE 3 with the other rinse operations. If a rinse operation is specified by the protocol for the block anyway, the default rinse is not scheduled because the probe will be warmed sufficiently by the scheduled rinse operation. The default rinse is scheduled when no rinse operation is otherwise scheduled and a specified probe idle time elapses. In preferred embodiment, the pre-warm rinse type (600 microliters) is executed by default.

FIG. 8 is a diagram illustrating the operation of the portion of the scheduler program used to determine the type of rinse and/or pre-warm operation to be scheduled at the start of the block in accordance with the description set forth above. The portions of the program code corresponding to the flow chart of FIG. 8 for performing the determination of the minimum interval can be found in Appendix 1 in SCHED2.LST starting at line 1176.

The method of the present embodiment described above, eliminates carryover of unknown analyte by commanding the performing of between block rinsing as part of the commands at the beginning of a block before the first aspirate or dispense steps in the block. The current block (not the previous block-different assay) determines the worse case carryover rinse appropriate for that block. This approach safeguards against unknown analyte carryover across one or more blocks.

The above method provides for reducing the amount of rinse solution used. When a block transition does not indicate a significant carryover concern, a lesser amount of rinse solution is used. Therefore, less rinse may be used overall thereby requiring that the rinse be replaced less frequently. Also, by using less rinse, less waste is generated.

With this aspect of the invention, the scheduling routine dynamically and adaptively determines the appropriate type of cleaning operation based upon the actual sequence of activities selected by the scheduler.

In alternative embodiments, the conditional cleaning command may be located at the end of a time block and be conditioned on the time block that succeeds the time block having the conditional rinse information. In a further embodiment, there may be conditional rinse information at both the beginning and the end of a time block and the rinse performed may be conditioned on one or the other rinse command, depending upon a priority, or on both.

In a further embodiment of the present invention, a "paneling" feature could be provided. With "paneling", separate patient samples would not have to be prepared when it is desired to run several different assays on the same patient's sample. To provide this feature, one or more disposable cartridges not containing any patient specimen sample could be loaded into the carousel rack in addition to the cartridge containers having patient specimen sample. The fluid moving system of the analyzer would then move portions of the patient's specimen sample from the one disposable in which it had been provided, and pipette it to the disposables not containing the patient's sample. Thus, the analyzer unit can relieve the operator or others from the need for preparing separate containers.

Although the present invention has been described in terms of a biological analyzer that operates automatically and unattended (e.g. in a "walk-away" mode in which the operator-user does not add or remove specimen during a run), it is understood that the present invention can readily be adapted to an "interruptable" mode analyzer in which the processing of the samples during a run can be interrupted so that an additional sample may be added. In such an analyzer, the processing program would modify the interrupted schedule so that the desired assay could be performed on the added specimen sample in a similar manner as if it were part of the original load list.

It is intended that the foregoing detailed description be regarded as illustrated rather than limiting and that it is understood that the following claims including all equivalents are intended to define the scope of the invention.

I claim:

1. An improved biological sample analyzer for conducting assays of samples loaded therein and which includes instrument systems for performing operations on each biological sample and a scheduling means for scheduling the operations of the instrument systems, the improvement comprising:
    (a) means for scheduling an adaptive cleaning operation prior to any scheduled instrument system operation; and
    (b) means for conducting the assays of the biological samples by performing the scheduled instrument system operations and performing a cleaning operation prior to any scheduled instrument system operation, said cleaning operation determined by the instrument system operation scheduled prior to said cleaning operation.

2. The improved biological analyzer of claim 1 in which the means for conducting an assay further comprises:
    means for conducting first and second assays of the biological samples wherein said first assay and said second assay are different assays.

3. The improved biological analyzer of claim 2 in which the means for scheduling a cleaning operation prior to performing a scheduled system operation further comprises:
    means for performing a first cleaning operation upon the condition that the instrument system operations immediately preceding said cleaning operation are of a first assay type, and
    means for performing a second cleaning operation upon the condition that the instrument system operations immediately preceding said cleaning operation are of a second assay type.

4. The improved biological sample analyzer of claim 1 further comprising:
    (a) means for scheduling a warming operation prior to an instrument system operation; and
    (b) means for conducting the assays of the biological samples by performing the scheduled instrument system operations and performing a warming operation prior to a scheduled instrument system operation determined upon a scheduled lapse of time between the scheduled instrument system operation and the instrument system operation scheduled prior thereto.

5. A biological sample analyzer for conducting assays of biological samples loaded therein comprising:
    (a) means for scheduling operations by instrument systems on each biological sample;
    (b) means for scheduling a conditional cleaning operation prior to any instrument system operation; and
    (c) means for conducting the assays of the biological samples by performing the scheduled instrument system operations and performing a cleaning operation prior to any scheduled instrument system operation, said cleaning operation conditioned upon the instrument system operation scheduled prior to said cleaning operation.

6. The biological analyzer of claim 5 further comprising:
    means for conducting first and second assays of the biological samples wherein said first assay and said second assay are different assays.

7. The biological analyzer of claim 6 in which the means for scheduling a conditional cleaning operation prior to performing a cleaning operation further comprises:
    means for performing a first cleaning operation upon the condition that the instrument system operations immediately preceding said cleaning operation are of a first assay type, and
    means for performing a second cleaning operation upon the condition that the instrument system operations immediately preceding said cleaning operation are of a second assay type.

8. The improved biological sample analyzer of claim 5 further comprising:
    means for scheduling a warming operation prior to an instrument system operation; and further in which the means for conducting the assays of the biological samples by performing the scheduled instrument system operations further comprises:
    means for performing a warming operation prior to a scheduled instrument system operation determined upon a scheduled lapse of time between the scheduled instrument system operation and the instrument system operation scheduled prior thereto.

9. An improved method of operating a biological sample analyzer for conducting assays of samples loaded and in which operations by instrument systems are scheduled to be performed on each biological sample, the improvement comprising the steps of:
    (a) scheduling a conditional cleaning operation prior to any scheduled instrument system operation; and
    (b) conducting the assays of the biological samples by performing the scheduled instrument system operations and performing a cleaning operation prior to any scheduled instrument system operation, said cleaning operation determined by the instrument system operation scheduled prior to said cleaning operation.

10. The improved method of claim 9 in which the step of conducting an assay further comprises:
    conducting first and second assays of the biological samples wherein said first assay and said second assay are different assays.

11. The improved method of operating a biological sample analyzer of claim 9 in which the step of scheduling operations by instrument systems further comprises the steps of:
    (a) developing time blocks for each sample for conducting operations to be performed by instrument systems for each specimen sample to perform the assay of said each sample; and
    (b) developing a schedule of the time blocks to be performed by the analyzer instrument systems on the samples;
    and in which the step of scheduling a conditional cleaning operation is characterized as further comprising the step of:
    scheduling a cleaning operation to be performed by an instrument system at a transition between time blocks from the developed schedule of time blocks.

12. The improved method of claim 11 in which the step of scheduling a cleaning operation is based upon the sequence of time blocks schedule.

13. The improved method of claim 12 in which the step of scheduling a cleaning operation is performed after all the time blocks of all the samples have been scheduled.

14. The improved method of claim 11 in which the step of performing a cleaning operation further comprises:

performing a first cleaning operation before a time block for a sample upon the condition that the time block is preceded by a time block of a first assay type, and performing a second cleaning operation before the time block for said sample conditioned upon the time block being preceded by a time block of a second assay type.

15. The improved method of claim 14 in which the step of performing cleaning operation is further characterized wherein the first assay type is the same assay type as being performed on said sample and the second assay type is an assay different from the assay type being performed on said sample.

16. The improved method of operating a biological sample analyzer of claim 9 for conducting assays of samples loaded therein further comprising the step of:

scheduling a warming operation prior to any instrument system operation; and in which the step of conducting the assays of the biological samples by performing the scheduled instrument system operations is further characterized by the step of:

performing a warming operation prior to a scheduled instrument system operation determined upon the lapse of time between the scheduled instrument system operation and the instrument system operation scheduled prior thereto.

17. A method of operating a biological sample analyzer for conducting assays of biological samples loaded therein comprising the steps of:

(a) scheduling operations by instrument systems on each biological sample;

(b) scheduling a conditional cleaning operation prior to any instrument system operation; and (c) conducting the assays of the biological samples by
(1) performing the scheduled instrument system operations, and
(2) performing a cleaning operation prior to any scheduled instrument system operation, said cleaning operation conditioned upon the instrument system operation scheduled prior to said cleaning operation.

18. The method of claim 17 in which the step of conducting the assays further comprises:

conducting first and second assays of the biological samples wherein said first assay and said second assay are different assays.

19. The method of claim 17 in which the step of scheduling operations by instrument systems is characterized as further comprising the steps of:

(a) developing time blocks for each sample for conducting operations to be performed by instrument systems for each specimen sample to perform the assay of the sample; and (b) developing a schedule of the time blocks to be performed by the analyzer instrument systems on the samples, said schedule including a sequence of time blocks;

and in which the step of scheduling a conditional cleaning operation is characterized as further comprising the step of:

scheduling a cleaning operation to be performed by an instrument system at a transition between time blocks from the developed schedule of time blocks.

20. The method of claim 19 in which the step of scheduling a cleaning operation is based upon the sequence of time blocks scheduled.

21. The method of claim 20 in which the step of scheduling a cleaning operation is performed after all the time blocks of all the samples have been scheduled.

22. The method of claim 21 in which the step of performing a cleaning operation further comprises:

performing a first cleaning operation before a time block for a sample upon the condition that the time block is preceded by a time block of a first assay type, and performing a second cleaning operation before the time block for said sample upon the condition that the time block is preceded by a time block of a second assay type.

23. The method of claim 22 in which the step of performing a cleaning operation further comprises:

performing a first cleaning operation before a time block for a sample upon the condition that the time block is immediately preceded by a time block of a first assay type, and performing a second cleaning operation before the time block for said sample upon the condition that the time block is immediately preceded by a time block of a second assay type.

24. The method of claim 23 in which the step of performing cleaning operation is further characterized wherein the first assay type is the same assay type as being performed on said sample and the second assay type is an assay different from the assay type being performed on said sample.

25. The method of claim 24 in which the step of performing a cleaning operation is further characterized as rinsing a pipette probe of the biological analyzer.

26. The method of operating a biological sample analyzer of claim 17 further comprising the step of:

scheduling a warming operation prior to any instrument system operation; and in which the step of conducting the assays of the biological samples by performing the scheduled instrument system operations is further characterized by the step of:

performing a warming operation prior to a scheduled instrument system operation determined upon the lapse of time between the scheduled instrument system operation and the instrument system operation scheduled prior thereto.

27. An improved method of operating a biological sample analyzer for conducting assays of biological samples loaded therein comprising the steps of:

(a) scheduling operations by instrument systems on each biological sample; and (b) conducting the assays of the biological samples by performing the scheduled instrument system operations and performing a warming operation prior to a scheduled instrument system operation, said warming operation determined upon the lapse of time between the scheduled instrument system operation and the instrument system operation scheduled prior thereto.

28. An improved biological sample analyzer for conducting assays of biological samples loaded therein comprising:

(a) means for scheduling operations by instrument systems on each biological sample; and (b) means for conducting the assays of the biological samples by performing the scheduled instrument system operations and performing a warming operation prior to a scheduled instrument system operation, said warming operation determined upon a lapse of time between the scheduled instrument system operation and the instrument system operation scheduled prior thereto.

29. The improved method of claim 28 in which the means for conducting an assay further comprises:
   means for conducting first and second assays of the biological samples wherein said first assay and said second assay are different assays.

* * * * *